United States Patent [19]

Albert

[11] 4,104,526

[45] Aug. 1, 1978

[54] GRID-CATHODE CONTROLLED X-RAY TUBE

[76] Inventor: Richard D. Albert, 317 Hartford Rd., Danville, Calif. 94526

[21] Appl. No.: 638,434

[22] Filed: Dec. 8, 1975

Related U.S. Application Data

[63] Continuation-in-part of Ser. No. 353,451, Apr. 24, 1973, Pat. No. 3,925,660, which is a continuation-in-part of Ser. No. 251,378, May 8, 1972, abandoned.

[51] Int. Cl.$^2$ ............................................. G03B 41/16
[52] U.S. Cl. .................................... 250/403; 250/402; 250/409
[58] Field of Search ............... 250/401, 402, 403, 404, 250/405, 408, 409, 355

[56] References Cited

U.S. PATENT DOCUMENTS

| | | | |
|---|---|---|---|
| 2,172,581 | 9/1939 | Horsley | 250/416 R |
| 2,878,393 | 3/1959 | Graves | 250/403 |
| 3,567,940 | 3/1971 | Lambert | 250/355 |
| 3,633,029 | 1/1972 | Duffy | 250/405 |
| 3,783,287 | 1/1974 | Fulton | 250/409 |
| 3,783,333 | 1/1974 | Atlee | 250/403 |
| 3,842,280 | 10/1974 | Herrick | 250/409 |
| 3,878,455 | 4/1975 | Ochmann | 250/416 R |

Primary Examiner—Craig E. Church

[57] ABSTRACT

An X-ray tube whose output may be measured and controlled through the grid-cathode combination is disclosed. Additionally, a method of an apparatus for controlling the X-ray production from the anode of such an X-ray tube over a known interval of time, either in steady state or pulse mode operation, is disclosed in this application. In a preferred form, the cathode of an X-ray tube is operated at a high negative potential so that the anode, including at least one target, may be operated near ground potential. Actual return current flow from the anode to the cathode is detected and used to control the control grid or cathode to produce either pulsing (say, 100 microseconds) or consistent anode current (up to several days, if desired), independent of spurious electron production in the X-ray tube. Additionally, means for assuring outgasing of an X-ray tube, particularly in the vicinity of the collimating and shielding means, surrounding the anode is disclosed.

15 Claims, 9 Drawing Figures

GRID-CATHODE CONTROLLED X-RAY TUBE

This application is a continuation-in-part of my application Ser. No. 353,451, filed Apr. 24, 1973, now U.S. Pat. 3,925,660, issued Dec. 9, 1975. which in turn was a continuation-in-part of my application Serial No. 251,378, filed May 8, 1972, now abandoned. The disclosure of said U.S. Pat. No. 3,925,660 is incorporated hereby in the present specification.

The present invention relates to x-ray tubes whose output is controlled by the grid to cathode potential. More particularly, it relates to a method of, and apparatus for, measuring the return current flow from the anode of such an x-ray tube to the high potential power supply connected between the anode and the cathode-control grid as an indication of actual x-ray production by the tube.

It is a particular object of the present invention to permit accurate measurement of x-ray production from an x-ray tube by measuring actual anode current flow independently of the input current to the cathode source producing electrons that are accelerated to bombard at least one target on the anode. In a preferred form of the invention, the anode is maintained at a low potential very slightly negative to ground and the measured anode current is used to control a high negative potential applied to the electron beam generating elements, including the cathode electron source and a control grid. In said preferred form, the potential between the control grid-cathode combination and the anode are regulated in an amount and to an extent necessary to hold the anode return current substantially constant over a given interval of time (from a few milliseconds to several days). In another form, the anode return current is used to pulse the cathode-grid so that the electron beam is cycled on and off in accordance with the sensed or measured anode current. Further, in accordance with the invention, a combination of such pulsing and stabilizing the anode return current is used with stepping or sequencing under computer control to set different and predeterminable anode current levels to generate x-rays of known energies from a single target or to generate polychromatic or monochromatic x-rays from either other primary or secondary targets associated with the anode.

In many x-ray tube applications it is desirable to maintain a constant x-ray output over intervals of time ranging from short (less than 1 ms) to long (hours to days) time intervals. When one is making analyses using x-rays or x-ray spectrographic determinations of unknown in a material sample, it is frequently necessary to duplicate the measurement conditions using a standard reference sample. The data must be obtained for both the unknown as well as the reference sample under reproducible conditions, i.e. with the same x-ray flux intensities and the same x-ray spectra.

Other applications requiring high x-ray output stability are for thickness monitoring in process control and for use with crystal spectrometers. Both of these measurements require a large number of repetitive irradiations of a material. The latter measurements must be repeated at a large number of Bragg angles to obtain the desired spectrum. Another useful application is for x-ray scanning of a human subject which must be accomplished with a constant intensity x-ray beam to obtain a high quality x-ray image.

The conventional means for controlling x-ray output is by stabilizing the current supplied to the filament of an x-ray tube. Typically, the filament is operated near ground potential and the anode is operated at a large positive potential. The filament current may thereby be monitored and controlled without the use of an isolation transformer. This technique suffers from some disadvantages; the filament may not respond in a reproducible fashion to changes in filament current due to the possibility of uneven emission caused by hot spots or other local effects in the filament material and the response is not as fast as may be desired if a fast pulsed x-ray output is desired.

There are reasons for using an indirectly heated cathode as a source of electrons in an x-ray tube. The filament may be operated at much lower temperature and produce the same electron emission as a filament source of electrons and the emission is much more evenly distributed at the source. The lower operating temperature and lack of hot spots result in a longer lifetime for the indirectly heated cathode x-ray tube. However, the time response of the latter is slower since a larger heat capacity is present due to the added cathode structure. The time response is greatly improved by the addition of a grid to control the emitted electrons from the cathode by means of varying the control grid potential. Other grids may also be added to control electron intensity and electron beam focussing as in the electron gun used in the common television set.

The grid of an electron gun used in an x-ray tube may be operated at near ground potential or at high negative potential. In the former case, the anode is at high positive potential and in the latter case, the anode is near ground potential. Either the electron emission current may be controlled or the current collected at the target or anode may be controlled. If the emission current is regulated, it is not necessary to provide high voltage isolation between grid and cathode since the voltage difference between them is relatively small. However, if the cathode end of the tube is operated at a high negative potential, it is necessary to provide isolation between the external current controls and the control grid. In this case the tube anode may be operated at ground which has some advantages in that closer coupling between the x-ray target and the material to be irradiated is possible since they are at nearly the same electrical potential. Also, since there is no need for electrical insulation between tube and ground, this facilitates heat transfer to an external heat sink.

In the present embodiment of the invention, the cathode is operated at high negative potential and the anode is operated near ground but not at ground. This leads to an x-ray tube having essentially all of the advantages of ground potential operation just mentioned but with the added advantage of being able to control and stabilize anode current which is more likely to be a true measure of x-ray output than emission current. This is because under some conditions it is possible for spurious electron emission to take place from the control grid or other gun and tube structures. The spurious emission may result from the effect of electric fields or from secondary electron emission caused by electron bombardment of these structures. The spurious electrons arising from these effects may produce x-rays if they are accelerated to the anode. Hence monitoring the electron current that directly impinges upon the target anode is a better measure of the x-ray output intensity. In the examples above the emission current would be less than the actual current collected by the anode. Other effects such as diversion of cathode current to parts of the tube than the anode could result in the emission current being larger than the actual anode current. These effects could be a result of arcing, glow discharge and leakage current paths being set up inside the x-ray tube.

The present x-ray source utilizes a means to sense the anode current directly through a sensing resistor and the sensed signal is detected by a current stabilizing circuit comprising an optical coupler which applies voltage variations to the control grid of the x-ray tube to stabilize the anode current. The optical coupler is required to stand off the high voltage between the high negative potential at the control grid and ground. If the x-ray tube were regulated by means of filament current, as in the case of x-ray tubes described in the prior art, it would be possible to use an isolation transformer rather than an optical coupler for high voltage isolation since the filament may be heated by alternating current. This is the typical mode for regulating the current of x-ray tubes. However, the deficiencies in filament regulation for stabilizing x-ray output, as described earlier, are there.

Briefly, the present invention is directed to an x-ray source having superior current regulation leading to improved x-ray output stability. The current collected by the anode of the x-ray tube is directly sensed by means of a sensing resistor in series with the tube anode thereby giving rise to a voltage signal which may be measured or fed back to the grid of the tube in the opposite sense so as to regulate the anode current of the tube. By regulating the anode current rather than the emission current from the cathode, it is possible to improve the regulation since the emission current may be diverted from the anode due to leakage currents, corona and other undesirable effects such as positive emission from other elements of the tube and its gun structure.

The x-ray tube may be operated with a negative voltage applied to its cathode or with a positive voltage applied to its anode. In the preferred embodiment of this invention the cathode is operated at negative high potential and the anode is operated near ground potential. This introduces several advantages which have been discussed in my pending patent application U.S. Ser. No. 353,451.

In order to sense the anode current directly, it is necessary to provide a means for feeding back the signal to the grid and maintain the necessary voltage isolation between anode and grid. The voltage that must be isolated is therefore essentially almost the full accelerating voltage between the cathode and the anode of the tube. In the present embodiment of the invention such isolation is provided by means of an optical coupler similar to that described in my application Ser. No. 353,451.

Further objects and advantages of the present invention will become apparent from the following detailed description taken in conjunction with the drawings which form a part of this specification.

Figures 1, 1A, 1B:
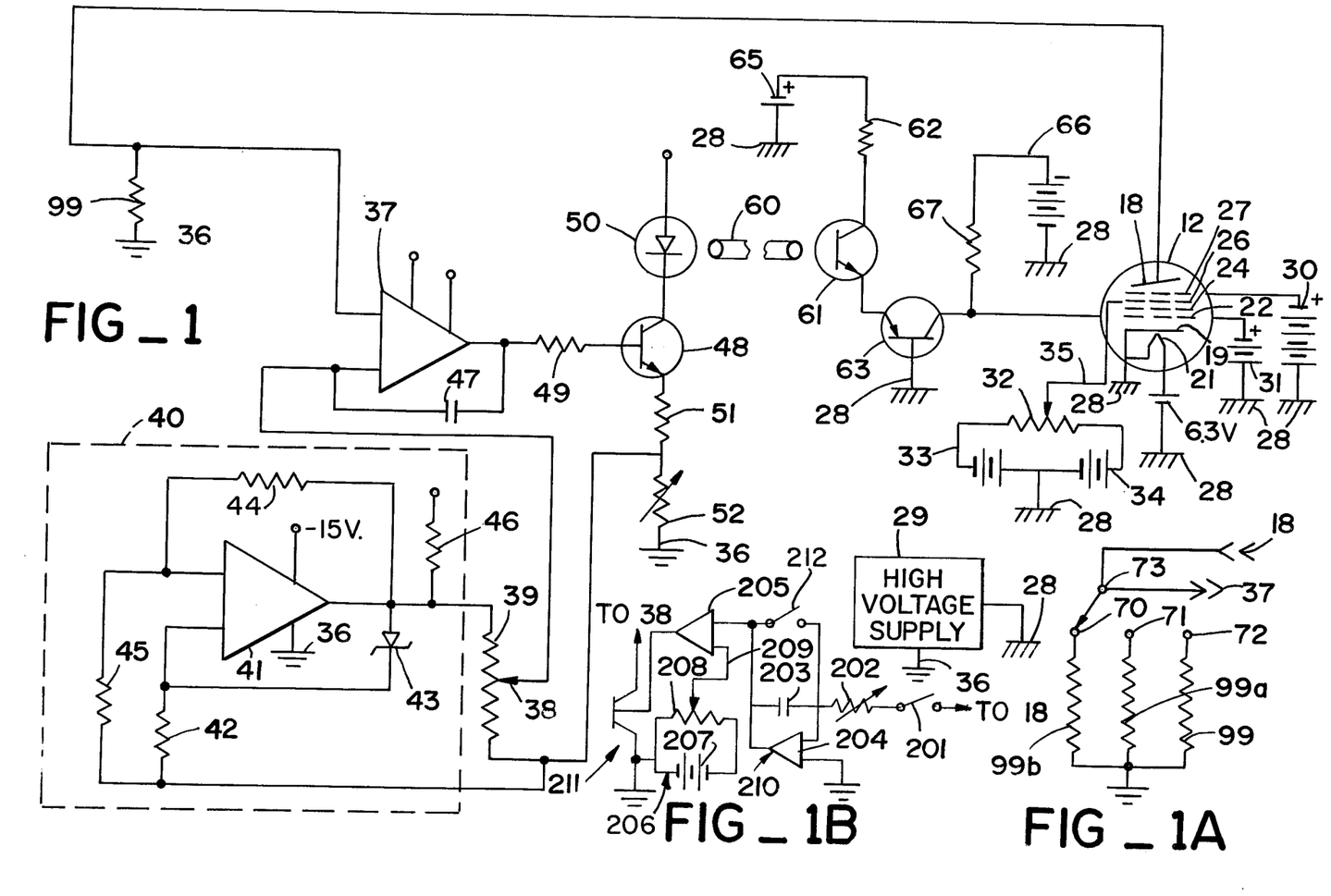
FIG. 1 is a schematic electrical diagram illustrating a preferred form of the measuring and control circuit for a grid-cathode controlled X-ray tube in accordance with the present invention.
FIG. 1A illustrates a range changing circuit useful in connection with the circuit of FIG. 1.
FIG. 1B illustrates an alternate circuit arrangement for pulse mode operation of the X-ray tube.

Operation of the X-ray source will be best understood by referring to FIG. 1. The X-ray tube is indicated schematically by the device 12 whose structure consists of a filament 21, indirectly heated cathode 19, control grid 22, first anode 24, focussing anode 26 and ultor 27. These elements comprise the electron gun and operate at voltages near a common voltage which is the negative output voltage of high voltage supply 29 whose output voltage is proportional to its input voltage. The output negative potential common point is indicated by the floating ground symbol designated by reference number 28.

Typically, the ultor voltage, supplied by battery 30, is set at about 5000 volts; the first anode voltage, supplied by battery 31, at about 150 volts; the focussing anode voltage supplied by the voltage divider consisting of resistor 32, batteries 33 and 34 and the variable tap 35 is set at a point between positive and negative 100 volts.

The electron beam strikes the target anode 18 and the tube current returns to true ground indicated by the symbol 36 through the resistor 99. The voltage developed across resistor 99 is applied to the non-inverting input of operational amplifier 37. The inverting input of opamp 37 is at a negative voltage determined by the center tap 38 of resistance divider potentiometer 39. This voltage is adjustable between almost ground and the negative 10 volts output of reference voltage supply 40.

The reference voltage supply 40 is of a standard type that has been published in the literature. Under equilibrium conditions, both of the inputs to operational amplifier 41 are approximately of equal voltage and the current through resistor 42 and zener diode 43 is regulated at a nearly constant value. The output voltage of negative 10 volts is determined by adjusting the ratio of the resistors 44 and 45, which are selected to track each other in value as the temperature is varied. This ratio is adjusted until a voltage equal to the difference between 10 volts and 8.6 volts (the zener has a threshold of 8.6 volts) is developed across resistor 42. Under these conditions, the current flowing through resistor 46 from the negative 15 volts supply generates a voltage drop of about 5 volts across resistor 46.

The nearly constant voltage output of reference supply 39 is tapped off by center tap 38 and applied to the inverting input of opamp 37 where it is compared with the x-ray tube current flowing through resistor 99. At equilibrium the inputs to opamp 37 are nearly equal. This results in stabilization of the x-ray tube current.

Operation of the remainder of the current stabilization part of the system will now be described. If the anode current of the x-ray tube decreases due to an instability, a positive voltage increase will appear at the output of opamp 37. This is the result of the noninverting input of opamp 37 becoming less negative. The high frequency portion of the signal appearing at the output of opamp 37 is cancelled by means of the feedback capacitor 47. This capacitor is included to suppress the tendency of the circuit to oscillate. The resulting signal is then applied to the base of transistor 48 through the current limiting resistor 49. As transistor 48 conducts a positive voltage is impressed across infra-red emitting diode 50 causing it to draw more current which is limited by current limiting resistor 51 so as to protect diode 50. As diode 50 draws more current, it emits more infrared light. The gain of this portion of the system is limited to improve stability by feedback of the voltage developed across variable resistor 52 to the inverting input of opamp 37.

The infra-red signal is transmitted by lightpipe 60 to the base of phototransistor 61 causing the photo tansistor 61 to conduct harder, thereby drawing more base current from pnp transistor 63 through collector resistor 62 to the voltage supply 65. The additional base current in transistor 63 makes it conduct harder and draw more collector current from voltage supply 66 through load resistor 67 and transistor 63 to the voltage supply 65. This results in a positive voltage swing at the grid 22 of x-ray tube 1.

Resistors and capacitors appearing in FIG. 1 without reference numbers are not essential to operation of the circuit. This is also true of the Ne 2 neon light. They provide transient and spark protection.

An extension of the current stabilizing effectiveness of this system over a larger range of current operation is achieved through the use of the range switch circuitry shown in FIG. 1A. This circuit permits insertion of any one of 3 selectable resistances between the x-ray tube anode 18 and true ground 36. When switch contact 73 is shorted to switch contact 72, the resistor 99 is connected between the anode 18 and ground. The voltage developed by the anode current across this resistor is applied to the noninverting input of opamp 37 as before. Anode current of 1 milliampere produces a voltage drop of 10 volts at the noninverting input of the opamp 37. A current of 1 milliamp is set by moving center tap 38 to the high voltage end of potentiometer 39. Thus, a variation of 10 microamps would correspond to an error of 1 percent or 100 millivolts at the input of opamp 37. If the switch means 73 is shorted to contact 71, then a resistance 99a, which has 10 times the value of resistor 99, is inserted between anode and ground. A variation of 10 microamps in anode current in this case corresponds to a 1 volt error signal at the input of opamp 37 which is a factor of 10 increase in error for the same variation in anode current. Thus, the stability for small current variations will be improved by a factor of 10 in absolute value although the relative value (percent stability) will not change. Similarly, when switch contacts 73 and 71 are shorted together, the relative value of stability will be the same as before, although the current being regulated is a factor of 10 less than the previously described case for the same centertap position along the potentiometer 39.

There are other means for sensing anode current than that described in the present embodiment of the invention. The anode resistor 39 may be removed so that the anode is directly shorted to ground. Then the current between anode and ground (the return current) may be sensed by detecting the magnetic field generated by it. A suitable device for sensing the field may be a magnetometer whose output is a D.C. voltage proportional to the magnetic field set up by the return current from the x-ray tube anode. An alternate means of sensing the magnetic field generated by the return current may be to apply it to the field coil of a generator in a motor-generator set.

FIG. 1b illustrates an embodiment of the invention suitable for operating in pulsed mode. In this arrangement, when the x-ray source is operated in pulsed mode, switch 201 must be closed. The voltage developed across anode resistor 99 due to return current of x-ray tube 12 is integrated by means of integrating circuit 210 comprising variable resistor 202, capacitor 203 and operational amplifier 204. The output of opamp 204 is directly proportional to the time integration of the voltage developed across resistor 202 and capacitor 203. Thus, the rate at which return current is integrated may be conveniently controlled by adjusting the value of resistor 202. The integrated signal output is applied to the noninverting input of digital comparator 205. At the inverting input of comparator 205, a voltage which is variable from the voltage source 206 is applied. Voltage source 206 comprises a battery 207, resistance divider 208 and center tap 209. When the output of integrator 210 exceeds the voltage at the center tap 209 the output of comparator switches to a high positive value which is impressed on the base of transistor 211. This causes transistor 211 to conduct thereby shorting the center tap 38 of the reference voltage source 40 to ground. The collector of transistor 211 is connected to this center tap 38. Thus the inverting input of opamp 37 is set at zero potential thereby cutting off the current of x-ray tube 12 as described previsouly with reference to the circuitry of FIG. 1.

The purpose for the presence of voltage divider 206 is to provide a means for setting the total amount of tube current to be integrated before the x-ray tube is shut off. This is a measure of the total number of x-rays produced during the time of operation starting from the closure of the switch 201 until the digital comparator 205 trips and shuts off the x-ray output.

The integrator is reset by first opening switch 201 and then closing switch 212 which discharges the integrating capacitor 203. The operation is restarted by reopening switch 212 and reclosing switch 201.

Figure 3A:
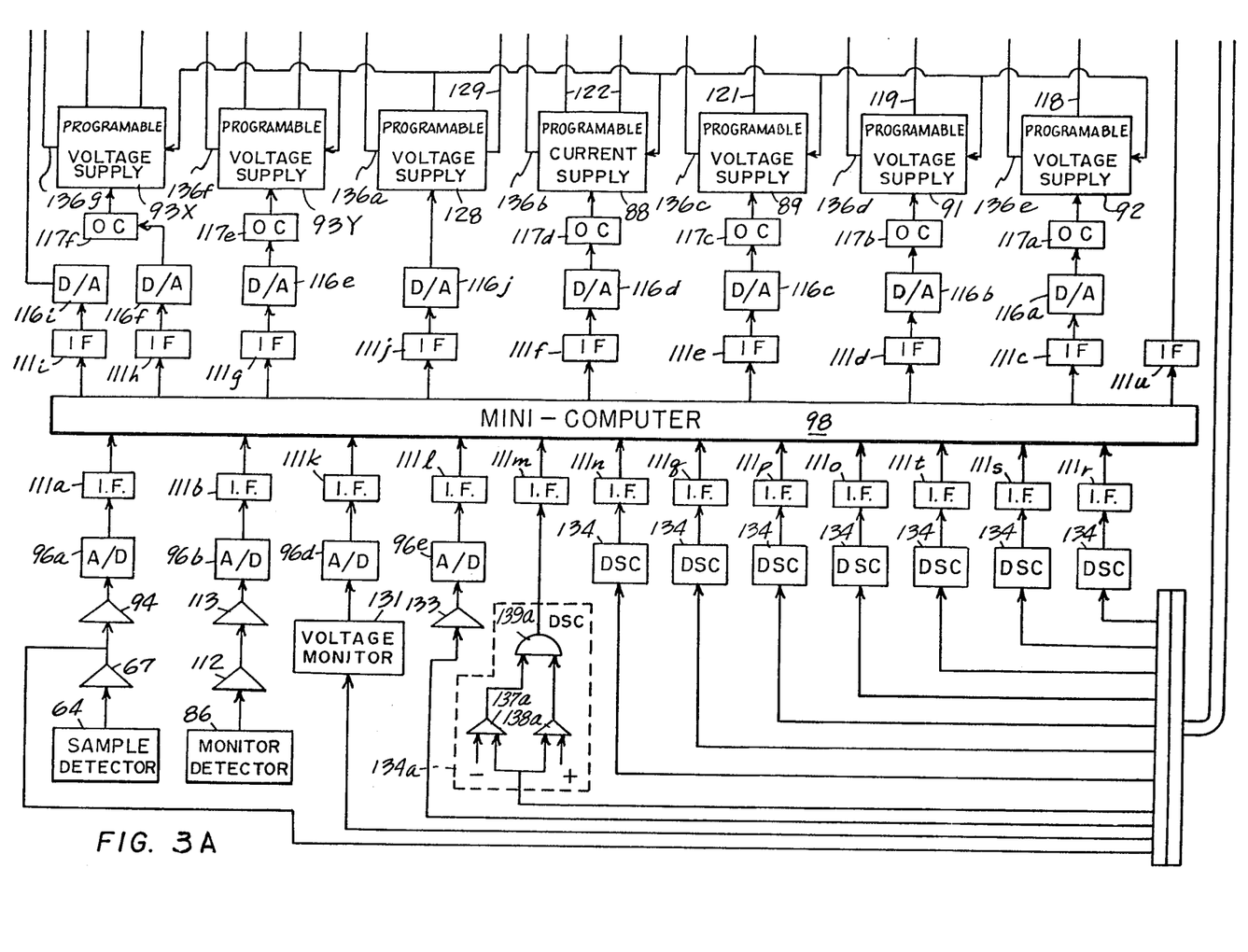
FIGS. 3A and 3B, which may be juxtaposed with FIG. 3B above FIG. 3A to form a single continuous circuit diagram, illustrates the details of a self-cycling feedback circuit for controlling the X-ray tube for automatic analysis of a substance with X-ray fluorescence spectroscopy.
Figure 3B:
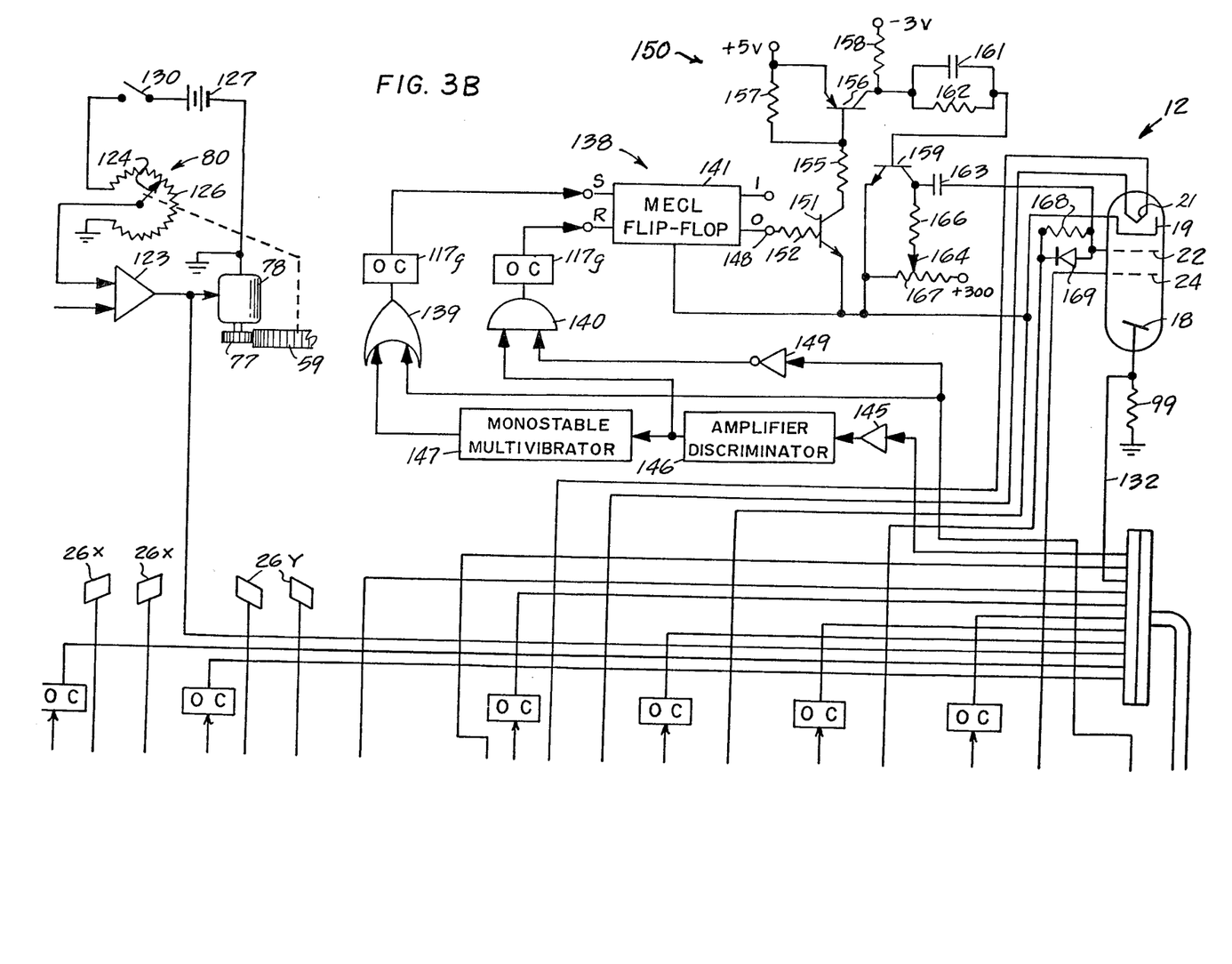

The optical couplers 117g of FIG. 3b are similar to the optical coupler shown in FIG. 1 which comprises an ME 7140 light emitting diode, a light pipe and an MRD 300 phototransistor. These are Motorola devices. However, to increase the speed of operation for use in the pulsing circuitry of FIG. 3b, the MRD 300 phototransistor should be replaced by a fast responding photodiode such as an MD2 which is a Monsanto device.

The interfacing of the optical couplers 117g into the pulsing circuitry of FIG. 3b is straightforward and would be easily performed by a person familiar with the art.

Alternatively, the optical couplers 117g may be replaced by a fast pulse transformer having suitable high voltage isolation. The speed of operation of the pulse circuitry should be about 300 nanoseconds or less preferably.

The integrator control circuit may be used either in the continuous or pulse mode of operation. Its use, combined with anode current sensing means, facilitates output of a precise dose of x-rays from x-ray tube 2 which can be set to any desired value. Uses are in applications where repeated, reproducible and consistent x-ray doses are required such as in thickness gauging, x-ray scanners for imaging or Bragg angle crystal spectrometers.

Figure 2:
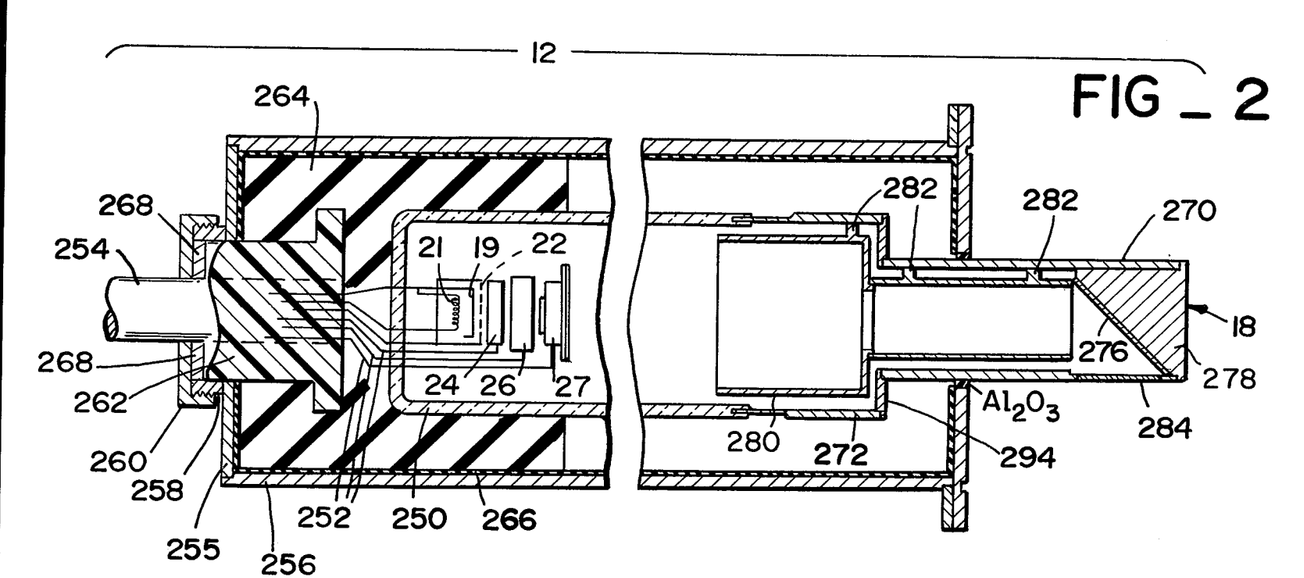
FIG. 2 is a side elevation view, partially in section of a grid-cathode controlled X-ray tube constructed for use in connection with the present invention.

Reference is now made to FIG. 2 wherein a preferred embodiment of the x-ray tube 12 is shown. In such a preferred embodiment, the electron generating elements are numbered as indicated schematically in FIG. 1. As seen in FIG. 2, filament 21, indirectly heated cathode 19, control grid 22, first anode 24, focussing anode 26, and ultor 27 are assembled is generally coaxial alignment with glass shell 250 and are supported therein by leads 252 which enter through high voltage cable 254 clamped to the end wall 255 of tube housing 256 by lock ring 258 and lock cap 260. Preferably, a high resistance flow path between leads 252 and end wall 255 is provided by adapter 262 formed of epoxy and the high dielectric strength material 264 filling the space between glass shell 250 and housing 256. As indicated, shielding, such as a lead lining 266 on the inner wall of aluminum housing 256 and washer 268 between cap 260 and adapter 262, is provided to suppress unwanted x-ray emission from this end of tube 12.

At the opposite end of tube 12, anode 18 is preferably formed by the tubular section designated as 270, suitably formed of copper, and fixed relative to glass shell 250 by stainless steel tubing 272 (sealed to glass shell 250) and collar 294. A particular advantage of forming anode 18 of tube 12 in this way is that with the front end having a considerably reduced diameter, it forms a probelike structure which permits closer coupling between the source of x-rays and the material to be irradiated. This results in a tighter and more efficient geometry between source, detector and sample. Another advantage of the end target probe design is to reduce the effect of scattered electrons and photons that reach the tube and gun structures to produce secondary x-rays that reduce the spectral purity of the tube x-ray output.

In the arrangement of FIG. 2, the target 276 is disposed at a 45 degree angle to the incident electron beam striking the end plug 278 of anode 18. Such a structure is made possible by forming plug 278 as a cylinder and then cutting it at a 45° angle. (Obviously, any other angle may be used.) Tubular section 270 and tubing 272 are desirably lined with a member 280 formed of low atomic number material, such as aluminum or the same material as target 276. As shown, tube 280 is formed to parallel the reduced and enlarged diameters. However, it will be noted (as further illustrated in FIG. 4) that a pump out space is maintained between member 280 and tube sections 270 and 272 by the stand-off lugs 282. The particular need for such pump-out channels is to permit complete out-gassing of the relatively heavy anode structure and the associated shielding and collimating means formed by tubular members.

As indicated, a side window for x-ray emissions is formed by a relatively thin beryllium plate 284.

Figure 2A:
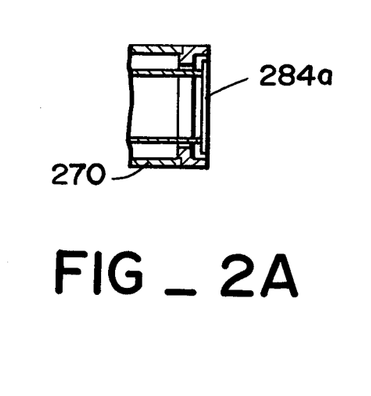
FIG. 2A shows an alternate construction of a single target arrangement for the anode of the tube shown in FIG. 2.

FIG. 2a illustrates an alternate end construction of tube 270, where the target 284a is mounted directly on a berylium window in the end of tube 270.

Figure 2B:
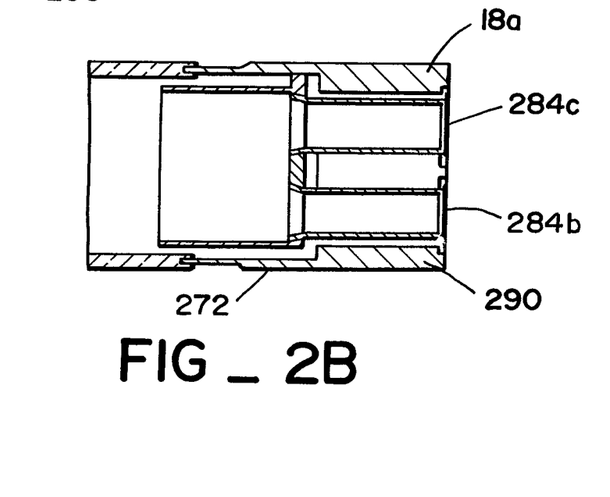
FIG. 2B shows a multi-target arrangement for the anode of the tube shown in FIG. 2.

FIG. 2b shows a further alternate for the end construction of tube 12. In this embodiment, at least two targets 284b and 284c are mounted on an enlarged diameter anode 290 forming a tubular extension of stainless steel tube 272. The shielding and collimating structure are similarly modified to accommodate the multiple targets.

Circuit provisions for adapting the system of FIG. 1 and 2 to automatic or self-cycling operation with the aid of a computer are shown in more detail in FIG. 3a and 3b. FIG. 3a may be disposed with FIG. 3b immediately above FIG. 3a to form a single continuous circuit diagram. In FIG. 3a and 3b, the legends "A/D" and "D/A" refer respectively to analog-to-digital and digital-to-analog converted circuits, suitable detailed constructions therefor being known in the art. Similarly, the legend "IF" refers to interface cards, also known to the art, for connecting digital signal channels of external circuitry with a computer. If, for example, the computer 98 is a minicomputer of the form identified as a PDP-11, manufactured by Digital Equipment Corporation, the interfaces IF may be of the DR11A form manufactured by the same company. The legend "OC" identifies optical coupling devices of the known form through which digital signals may be transmitted from one device to another without requiring direct electrical connection therebetween and which are used for isolation where the signal receiving circuit is at a high voltage level relative to the signal input circuit. The legend "DSC" refers to device status circuits of a form which will be hereinafter described.

Referring now to FIG. 3a and 3b in conjunction, fluorescent x-ray counts from a sample detector 64 are initially amplified by a preamplifier 67 and further amplified by amplifier 94 and then transmitted to an analog-to-digital signal converted 96 which codes each count signal according to pulse height for transmission to a computer 98 through an interface 111a. Accordingly, with suitable programming, the computer 98 is enabled to store a count of the number of fluorescent x-rays from a sample of each specific wavelength to establish the characteristic wavelength spectrum of fluorescent x-rays from the sample. Counts from the several monitor detectors 86, of which only one is depicted in FIG. 3A, are similarly transmitted through a preamplifier 112, amplifier 113, analog-to-digital converter 96b, and interface 111b.

Computer 98 is enabled to control the first anode voltage at x-ray source 12 through an interface 111c, digital-to-analog converter 116a, and optical coupler 117a which jointly form a control signal channel to the previously described programmable voltage supply 92. Supply 92 has a controlled voltage output 118 connected to the first anode 24 of the source. Similarly, the programmable voltage supply 91, having a controlled voltage output 119 coupled to the source control grid 22, is responsive to computer instructions received through an interface 111d, digital-to-analog converter 116b, and optical coupler 117b. Another interface 1113, digital-to-analog converter 116c, and optical coupler 117c enable the computer to control programmable voltage supply 89 which has a controlled voltage output 121 connected to the cathode 19 of the x-ray source 12. The computer is enabled to control the filament current of the source through an interface 111f, digital-to-analog converter 116d, and optical coupler 117d, the supply 88 having a pair of controlled current conductors 122 connected across the filament 21 of the source.

Control of electron beam deflection within the source 12 by the computer is enabled by an interface 111g, digital-to-analog converter 116e, and optical coupler 117e forming a control signal path to programmable voltage supply 93Y which has a pair of controlled voltage outputs connecting with a first pair of the opposed deflection plates 26Y. Similarly, an interface 111h connects with a digital-to-analog converter 116f which in turn connects through an optical coupler 117f with programmable voltage supply 93X which has a pair of controlled voltage outputs connected to the remaining pair of opposed deflection plates 26X, thus enabling primary target selection within source 12 by the computer.

To enable secondary target selection, an interface 111i connects the computer with a digital-to-analog converter 116i having an output connected to one input of a comparator 123, the output of which is connected to servomotor 78 to supply operating current thereto. Accordingly, servomotor 78 will operate to rotate secondary target table 59 if there is an output from comparator 123. To enable the voltage level supplied to the comparator 123 from digital-to-analog converter 116i to determine the rotational position of table 59, the other input of the comparator is connected to a rotatable tap contact 124 which is turned by servomotor 28 in synchronism with table 59. Rotatable tap 124 is in sliding contact with a circular resistor 126 having a DC voltage source 127 connected thereacross in series with an on-/off switch 130. With switch 130 closed, the voltage at rotatable contact 124 is a function of the rotational position thereof and this voltage is supplied to the other input of comparator 123. The comparator 123 will produce an output, causing motor 78 to operate, until such time as rotation of the contact 124 brings the voltage applied to comparator 123 from contact 124 into balance with the control voltage applied thereto from digital-to-analog converter 116i at which point the output of the comparator ceases and motor rotation stops.

The basic reference voltage, between the high voltage end of x-ray source 12 and ground, with reference to which the several programmable supplies 88, 89, 91, 92 and 93 provide selected voltage variations, is itself determined by an additional main programmable voltage supply 128 having an output coupled to each of the other programmable supplies. Main supply 128 is itself controllable by instructions from computer 98 through an interface 111j and digital-to-analog converter 116j. No optical coupler is employed in the last described instruction channel, as the main voltage supply 128 is of the known form having internal means providing isolation of the output from the signal receiving input components which operate at relatively low voltages.

In order to control the x-ray source 12 and servomotor 78 to obtain optimum speed and accuracy of the sample analysis, it may be desirable to provide the computer 98 with certain additional input information for reference purposes. For example, the computer may be enabled to monitor various significant source operating voltages to determine if these conform with the instructions issued by the computer and to enable corrective modifications in instructions if needed. For this purpose, the main programmable voltage supply 128 has a monitor output 129 which is coupled to a voltage monitor 131. The output of monitor 131 is transmitted to the computer through an analog-to-digital converter 96d and interface 111k. Similarly, a voltage signal indicative of electron beam current within the x-ray source 12 is provided to the computer through a conductor 132 connected between end anode 118 and an amplifier 133 having an output coupled to analog-to-digital converter 96e which in turn provides the digitized beam current information to the computer through an interface 111l.

To inform the computer if any of the outputs of the several programmable voltage and current supplies or the servomotor control comparator 123 are out of conformity with the instructions being applied thereto, which condition occurs momentarily following a change of instructions, a series of device status circuits 134 are employed. A first such device status circuit 134a detects any departure of the output voltage of the main programmable voltage supply 128 from that indicated by the control signal currently being received from the associated digital-to-analog converter 116j. Programmable voltage supplies 128 of this form have an error signal output 136a on which a signal appears whenever there is a discrepancy between the input instructions and output voltage. Error signal terminal 136a is coupled to the input of the device status circuit 134a which has an output coupled to the computer through an interface 111m.

The device status circuit 134a has a pair of digital output comparators 137a and 138a each having the main voltage supply error signal 136 connected to one input. A small negative voltage is applied to the other input of one comparator 137a while a small positive reference voltage is applied to the other input of the other comparator 138a. Thus, if the error signal from main voltage supply terminal 136a remains within the narrow limits defined by the small positive and negative voltages, the outputs of both comparators 137a and 138a are high. If the error signal increases significantly in either direction, the output of one of the comparators goes low. The outputs of the two comparators 137a and 138a are connected to the inputs of an AND gate 139a, the output of which is coupled to the interface 111m. The output of the AND gate 139a is high when the received error signal is within the acceptable narrow limits and goes low to inform the computer when a significant degree of error is detected.

Similarly, the error signal outputs 136b and 136g of programmable supplies 88, 89, 91, 92, 93Y and 93X, respectively, are each coupled to a separate one of a series of device status circuit 134 which are in turn coupled to the computer 98 through interfaces 111n, 111o, 111p, 111q, 111r, and 111s, respectively. For similar purposes, the output of servomotor control comparator 123 connects with an additional device status circuit 134 and interface 111t to inform the computer when the secondary target table 59 is undergoing movement.

Speed and accuracy of the system can be greatly enhanced if the generation of X-rays by source 12 is temporarily interrupted during periods when any significant operating parameter is temporarily out of conformity with the instructions supplied by computer 98 and also during the period required to process each X-ray count produced by sample detector 64. A source pulsing circuit 138 is provided for this purpose.

Pulsing circuit 138 utilizes an OR gate 139 and an AND gate 140 having outputs coupled respectively to the set and reset inputs of an MECL-type flip-flop 141 through optical coupler 117g. To reset the flip-flop upon detection of an X-ray by sample detector 64, the output of preamplifier 67 is coupled to one input of AND gate 140 through an isolating amplifier 145 and discriminator amplifier 146. As will hereinafter be described in more detail, resetting of flip-flop 141 blocks X-ray production in source 12. To enable the computer to override the pulsing circuit 138 and maintain X-ray production when that is desirable, the other input of AND gate 140 is controllable by the computer through an interface 111u and inverter 149.

Setting of the flip-flop to restore X-ray production after a predetermined period sufficient to process a detected X-ray is accomplished through a connection from the output of amplifier 146 to one input of OR gate 139 through a time delay means such as a monostable multivabrator 147. The other input of OR gate 139 is coupled to the computer through interface 111u to enable the computer to maintain x-ray production when necessary by overriding the pulsing circuit 138.

A single one of the outputs of flip-flop 141 is utilized to control pulsing of the X-ray source 12, this being the output 148 which is high when the flip-flop is in the reset state indicating that a count has been detected or that one or more operating parameters are incorrect as described above. This high condition of flip-flop output 148 is caused to block temporarily the electron beam generation within source 12 by applying a negative voltage pulse to control grid 22 relative to cathode 19. For this purpose, the output voltage at flip-flop output terminal 148, which is unipolar, is amplified and made bipolar by a circuit 150.

Circuit 150 may be formed of a first transistor 151 having a base coupled to flip-flop output 148 through a resistor 152 and having an emitter coupled to cathode 19. The collector of transistor 151 is coupled to the base of a second transistor 156 through a resistor 155. A small positive voltage, typically 5 volts, is applied to the emitter of transistor 156 and is also applied to the base thereof through a resistor 157. A small negative voltage, typically 3 volts, is applied to the collector of transistor 156 through a resistor 158, the collector of transistor 156 being coupled to the base of a third transistor 159 through a speed-up filter circuit formed by a parallel capacitor 161 and resistor 162. The emitter of transistor 159 is coupled to cathode 19 while the collector thereof is coupled to control grid 22 through a capacitor 163. The collector of transistor 159 is also connected to the movable contact 164 of a potentiometer through a resistor 166. A positive voltage, typically +300 volts, is applied to the resistive element 167 of the potentiometer which has one end connected to cathode 19. The previously described connection of controlled voltage output 119 of programmable voltage supply 91 to control grid 22 is made through a resistor 168 and a diode 169 which is in parallel therewith for D. C. restoration. It should be understood that the voltages referred to in the foregoing description of circuit 149 are voltages taken relative to the basic high negative voltage at the cathode end of X-ray source 12 and are additive thereto.

During the periods that an electron beam is being produced in source 12 to generate x-rays, output 148 of flip-flop 141 is low and thus transistor 151 is biased off and transistors 156 and 159 are also biased off. Under this condition, the voltage applied to control grid 22 is determined wholly by supply 91 and acts to draw electrons from cathode 19 to form the desired electron beam. Upon receipt of a reset pulse at flip-flop 141 from AND gate 140 indicating that a sample count is being processed, output 148 of the flip-flop goes high. Transistor 151 is turned on thereby turning on transistors 156 and 159. The resultant conduction through transistor 159 reduces the positive voltage on capacitor 163. This applies a negative step voltage at control grid 22 relative to cathode 19 thereby cutting off the electron beam within source 12. Upon setting of the flip-flop 141 by receipt of the delayed set pulse from OR gate 139, following expiration of a predetermined count processing time, flip-flop- output 148 again goes low turning off transistor 151. This turns off transistors 156 and 159 to restore the original voltage relationship between control grid 22 and cathode 19 thereby regenerating the electron beam in the X-ray source 12.

In the embodiment shown in FIG. 3b, the pulse signal is applied to the input of amplifier 145 as described previsouly. To operate in continuous fashion, the pulsed operation is disabled by applying a positive logic signal to the input of amplifier 149 as described previously.

Figure 4:
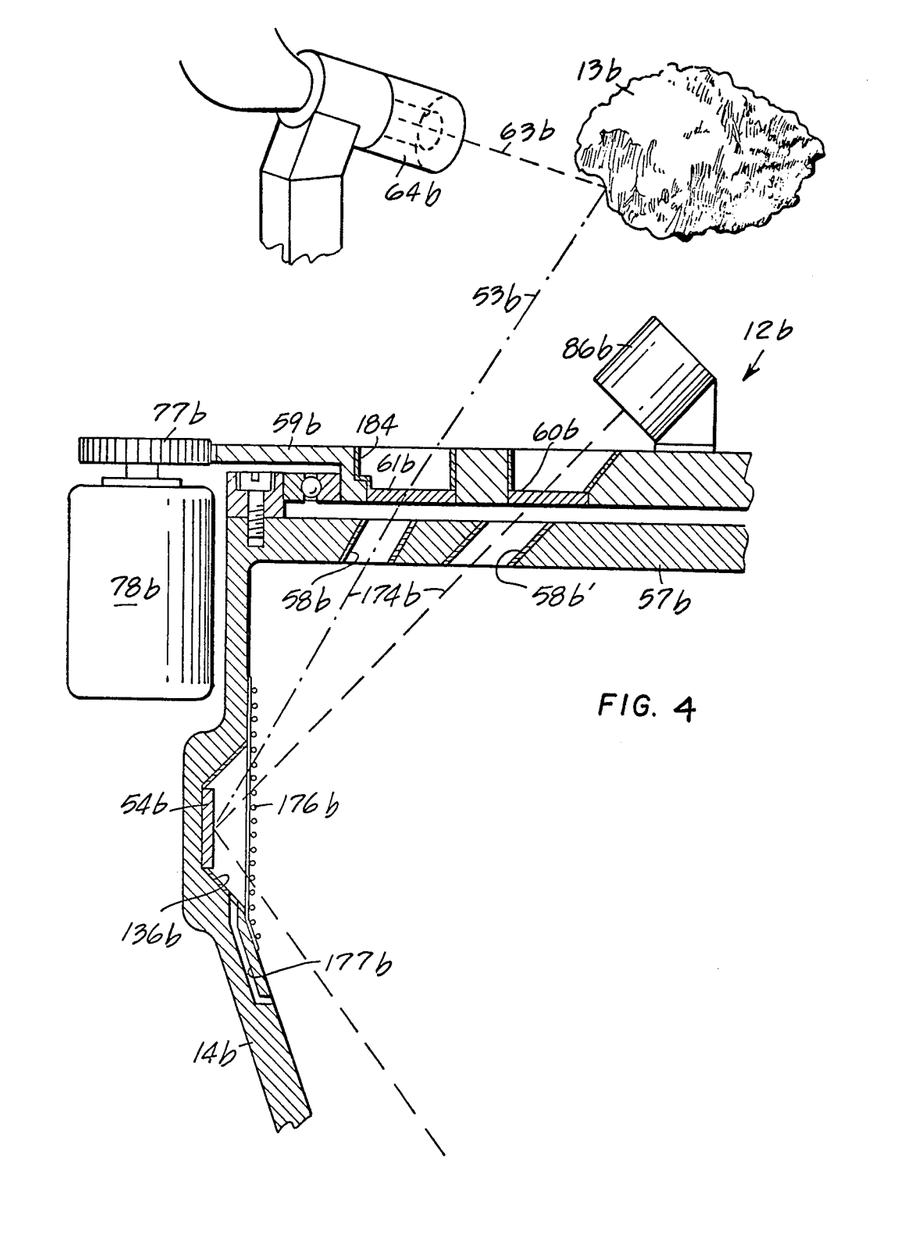
FIG. 4 illustrates an alternate target arrangement for an X-ray tube anode.

Another suitable geometry for the X-ray source 12 is illustrated in FIG. 4. This embodiment provides for backward angle X-ray emission from the primary targets 54b in conjunction with forward emission from the secondary targets 61b. The primary targets 54b may be mounted in cavities 173b in the sidewall of housing 14b in a manner similar to that described with reference to the preceding embodiment. Thus, a protective foil and grid 176b may be disposed across each cavity 173b and a pump out channel 177b communicates therewith. Primary X-rays 174b from the selected primary target 54b are transmitted through a passage 58b in collimating structure 57b to impinge upon a selected one of the secondary targets 61b, each of which is mounted in a well 184 in a table 59b which may be rotated by a servomotor 78b as previously described. The secondary targets 61b are disposed transversely in the wells 184 so that secondary fluorescent x-rays 53b are emihted from the side of the secondary target which is opposite from the side that receives the primary X-rays 174b. In this embodiment, the monitor detectors 86b may be mounted on table 59b in position to view secondary X-rays emitted from duplicate secondary targets 60b also carried on the table 59b in alignment with additional colli- Although only a few embodiments have been shown and described, various other modifications will become apparent to those skilled in the art from the foregoing specification. All such modifications coming within the scope of the appended claims are intended to be included therein.

What is claimed is:
1. Apparatus for pulsing the current output of an X-ray tube over a given time interval to produce a measurable value of anode current that is indicative of actual X-ray production by said tube, said tube having a single anode including at least one target adapted to generate X-rays upon bombardment by an electron beam, and electron gun means including a cathode for generating said electron beam and a control grid for modulating or suppressing substantially the entire electron flow from said cathode to said single anode, said electron gun means being positioned at the opposite end of an evacuated tube containing said anode, comprising
    a high potential source,
    means for applying relatively high negative potentials to said cathode and said control grid from said source,
    means for connecting said single anode to the ground side of said high potential source,
    means for detecting return current flow from said anode through said connecting means to said ground side of said high potential source as a measure of actual X-ray production during said given time interval, and means for controlling the potential difference between said cathode and control grid in accordance with said return current flow from said anode as a measure of actual X-ray production during said given time interval.

2. Apparatus in accordance with claim 1 wherein said control means includes means for pulsing the potential between said cathode and said control grid to pulse said electron beam on and off and said detecting means includes means for determining the total charge accumulated through said current flow detecting means in accordance with the number of pulses.

3. Apparatus in accordance with claim 2, wherein said pulsing means includes optical coupling means for controlling the potential between said control grid and said cathode.

4. Apparatus in accordance with claim 3, wherein said optical coupling means gates said potential through bi-stable circuit means connected in circuit with said control grid and said cathode.

5. Apparatus for controlling the input of an X-ray tube over a given time interval to produce a measurable value of anode current that is indicative of actual X-ray production by said tube, said tube having a single anode including at least one target adapted to generate X-rays upon bombardment by an electron beam, and electron gun means including a cathode for generating said electron beam and a control grid for modulating or suppressing substantially all electron flow between said cathode and said single anode, said electron gun means being positioned at the opposite end of an evacuated tube containing said single anode, comprising
 a high potential source,
 means for applying relatively high negative potentials to said cathode and said control grid from said source,
 means for connecting said single anode to the ground side of said high potential source,
 means for detecting return current flow through said anode ground connecting means to said high potential source, and
 means to control the control grid to cathode potential difference from said high potential source output in response to the return current flow from said single anode to said high potential source as a measure of actual X-ray production during said given time interval.

6. Apparatus in accordance with claim 5 wherein said control means regulates the potential difference between said cathode and said control grid to maintain said anode current constant over said given time interval to compensate for spurious variations in electron flow to said single anode.

7. Apparatus in accordance with claim 6, wherein said potential difference between said cathode and control grid is controlled by optical coupling means connected between the relatively low voltage return current sensing means and said cathode and control grid, said optical coupling means including an optical energy transmitter, an optical detector, and a light pipe therebetween to provide high voltage standoff between said transmitter and said detector.

8. Apparatus in accordance with claim 5, wherein said current flow detecting means is a resistor connected between said single anode and ground.

9. Apparatus in accordance with claim 5, wherein said means for connecting said single anode to the ground side of said high potential source includes means for maintaining said anode at a relatively high positive potential relative to actual ground potential.

10. A method of controlling the output of an X-ray tube to a consistent value over a given time interval, comprising the steps of positioning electron beam generating elements, including electron gun means having at least a cathode and a control grid, adjacent one end of an evacuated tube, positioning a single anode having at least one X-ray producing target thereon at the opposite end of said evacuated tube and remote from said electron beam generating elements, applying with respect to the single anode a predeterminable high negative potential relative to said cathode and said control grid to respectively generate and control an electron beam,
 sensing at least a portion of the return current from said single anode to ground potential during electron beam flow, and over said given time interval, controlling said high negative potential difference on at least one of said electron beam generating elements in a direction and to an extent necessary to maintain said current flow substantially constant during X-ray production from said target on said single anode to compensate for spurious variations in electron flow to said single anode.

11. An X-ray source comprising:
 a vacuum envelope;
 at least one anode element having at least one surface within said envelope for producing X-rays therefrom in response to electron bombardment;
 at least one electron gun means disposed within said envelope in spaced apart relationship from said anode element;
 said electron gun means including an electron emissive cathode element and a control grid element, said control grid element being disposed between said cathode element and said one anode element for controlling substantially all electron current flow from said cathode element to said anode element;
 a high voltage supply means for accelerating electrons from said cathode element to said one anode element at X-ray generating potentials connectable between said one anode element and one element of said electron gun means;
 a grid-cathode voltage supply means coupled between said cathode element and said control grid element to establish a voltage difference therebetween, one end of said grid-cathode voltage supply means being connected in common to one end of said high voltage supply means;
 said grid-cathode voltage supply means having an input control means to which control signals may be applied to vary selectively the magnitude of said voltage difference between said cathode element and said control grid element;
 means responsive to electron current flow from said cathode element to said anode element for generating control signals representative of the magnitude of said electron current flow; and
 means for applying said control signals to said input control means in a direction and to an extent necessary to maintain the electron current flow from said cathode element to said anode element at a predetermined value;
 said input control means including optical coupler means between said electron current flow responsive means and said grid-cathode voltage supply means for electrically isolating said grid-cathode supply means from the other end of said high voltage supply means.

12. An X-ray source as defined in claim 11 wherein said input control means includes means for setting a predetermined value of the electron current flow from said cathode element to said anode element.

13. An X-ray source as defined in claim 12 wherein said electron current flow setting means includes means for producing a set signal for at least temporarily suppressing X-ray production by said X-ray source, and further comprising:

beam suppression means coupled to at least one of said cathode element and said control grid element for altering said voltage difference therebetween to at least temporarily suppress said electron current flow; and a regenerative feed back bistable circuit means having an output coupled to said beam suppression means, said bistable circuit means having a first stable condition at which said beam suppression means is inactivated and having a second stable condition at which said beam suppression means is activated and having a set signal input for receiving a set signal which establishes said second stable condition for at least a predetermind time period, said set signal input being coupled to said control signal source through said optical coupler means to receive said set signal therethrough.

14. An x-ray source as defined in claim 11 further comprising means for maintaining said elements of said electron gun means at a high negative potential and said anode element substantially at electrical ground potential.

15. An X-ray source as defined in claim 14 wherein said means for maintaining said anode element substantially at ground potential comprises a low value electrical resistance connected between said anode element and ground for generating said control signals representative of the magnitude of said electron current flow, and said control signals are applied to said control grid element through said optical coupler means for varying said voltage difference between said cathode element and said control grid element in response to variations of voltage across said resistance to maintain said electron current flow at a predetermined value.

* * * * *